(12) United States Patent
Lee et al.

(10) Patent No.: US 9,142,784 B2
(45) Date of Patent: Sep. 22, 2015

(54) HIGHLY EFFICIENT CARBAZOLE-BASED COMPOUND, AND ORGANIC ELECTROLUMINESCENCE DEVICE COMPRISING SAME

(75) Inventors: Jun Yeob Lee, Seongnam-si (KR); Soon Ok Jeon, Seoul (KR); Hyo Suk Son, Seongnam-si (KR); Kyoung Soo Yook, Yongin-si (KR); Sang Eok Jang, Seoul (KR)

(73) Assignee: SK CHEMICALS CO., LTD., Gyeonggido (KR)

( * ) Notice: Subject to any disclaimer, the term of this patent is extended or adjusted under 35 U.S.C. 154(b) by 371 days.

(21) Appl. No.: 13/807,504

(22) PCT Filed: Jun. 23, 2011

(86) PCT No.: PCT/KR2011/004584
§ 371 (c)(1),
(2), (4) Date: Dec. 28, 2012

(87) PCT Pub. No.: WO2012/002671
PCT Pub. Date: Jan. 5, 2012

(65) Prior Publication Data
US 2013/0119367 A1    May 16, 2013

(30) Foreign Application Priority Data
Jun. 29, 2010 (KR) .................. 10-2010-0061704

(51) Int. Cl.
*H01L 51/00* (2006.01)
*C07F 9/6558* (2006.01)
(Continued)

(52) U.S. Cl.
CPC .......... *H01L 51/0072* (2013.01); *C07F 9/5728* (2013.01); *C07F 9/65583* (2013.01); *C09K 11/06* (2013.01); *H01L 51/5056* (2013.01);
(Continued)

(58) Field of Classification Search
None
See application file for complete search history.

(56) References Cited

U.S. PATENT DOCUMENTS

2007/0262704 A1    11/2007  Tsai et al.

FOREIGN PATENT DOCUMENTS

| KR | 10-2006-0109524 | 10/2006 |
| KR | 10-2007-0107007 | 11/2007 |

(Continued)

OTHER PUBLICATIONS

Jiang et al. (Org. Lett. 2001, 13(12), p. 3146).*

(Continued)

*Primary Examiner* — J. L. Yang
(74) *Attorney, Agent, or Firm* — Lucas & Mercanti, LLP

(57) ABSTRACT

The present invention relates to a highly efficient carbazole-based compound and to an organic electroluminescence device including the same. According to the present invention, provided are a compound for an organic electroluminescence device and an organic electroluminescence device including the compound, in which a carbazole-based phosphine oxide compound, which is a compound intended for an organic electroluminescence device, is employed to overcome the problems of conventional compounds for organic electroluminescence devices, i.e. those of instable thermal stability and low efficiency, and particularly, the compound of the present invention exhibits superior efficiency in pure-blue phosphorescent devices.

11 Claims, 2 Drawing Sheets

(51) Int. Cl.
  *C07F 9/572* (2006.01)
  *H01L 51/50* (2006.01)
  *C09K 11/06* (2006.01)
  *H05B 33/14* (2006.01)
(52) U.S. Cl.
  CPC ............ *H01L 51/5092* (2013.01); *H05B 33/14* (2013.01); *C09K 2211/1007* (2013.01); *C09K 2211/1014* (2013.01); *C09K 2211/1029* (2013.01); *H01L 51/0085* (2013.01); *H01L 51/5016* (2013.01)

(56) References Cited

FOREIGN PATENT DOCUMENTS

KR    10-2008-0080513    9/2008
KR    10-0938524 B1    1/2010

OTHER PUBLICATIONS

Xiuyu Cai, et al., Electron and Hole Transport in a Wide Bandgap Organic . . . , Applied Physics Letters, vol. 92, 2008.

* cited by examiner

HIGHLY EFFICIENT CARBAZOLE-BASED COMPOUND, AND ORGANIC ELECTROLUMINESCENCE DEVICE COMPRISING SAME

CROSS-REFERENCE TO RELATED APPLICATIONS

This application is a 371 of PCT/KR2011/004584, filed on Jun. 23, 2011, which claims the benefit of Korean Patent Application No. 10-2010-0061704, filed on Jun. 29, 2010, the contents of each of which are incorporated herein by reference.

TECHNICAL FIELD

The present invention relates to a highly efficient carbazole-based compound, which is capable of improving low efficiency characteristics of a conventional organic electroluminescence device, in particular, low efficiency characteristics of a pure-blue phosphorescent device, and to an organic electroluminescence device including the same.

BACKGROUND ART

Organic electroluminescence devices have a simpler structure, various processing advantages, higher luminance, superior viewing angle, quicker response rate, and a lower operating voltage than other flat panel display devices such as liquid crystal displays (LCDs), plasma display panels (PDPs), field emission displays (FEDs), etc., and thus many attempts are being made to use them as a light source of flat panel displays such as wall-mountable TVs or of the backlight units of displays, illuminators, advertisement boards and the like.

Typically, when direct-current voltage is applied to an organic electroluminescence device, holes injected from an anode and electrons injected from a cathode recombine to form electron-hole pairs, namely, excitons, after which the excitons return to a stable ground state and the corresponding energy is transferred to a light-emitting material and is thereby converted into light.

In an effort to increase efficiency and stability of an organic electroluminescence device, since C. W. Tang et al. of Eastman Kodak Company made an organic electroluminescence device operating at low voltage by forming a tandem thin organic film between two opposite electrodes (C. W. Tang, S. A. Vanslyke, Applied Physics Letters, vol. 51, pp. 913, 1987), thorough research into organic materials for organic electroluminescence devices with multilayered thin-film structures is ongoing. The lifetime of such a tandem organic electroluminescence device is closely related to the stability of the thin film and the material. For example, when the thermal stability of the material is lowered, the material may crystallize at high temperature or even at the operating temperature, undesirably shortening the lifetime of the device.

A variety of known compounds function as the conventional host materials of organic electroluminescence devices. These include triazine-based compounds, oxadiazole-based compounds, benzimidazole-based compounds, phenyl pyridine-based compounds, and silicon-based compounds. However, such compounds are problematic because superior efficiency characteristics cannot be achieved in the organic electroluminescence devices, and host materials able to exhibit superior characteristics in blue phosphorescent devices are considerably limited. Hence, the development of novel compounds to solve such problems is required.

As a novel host material, a novel phosphine oxide-based compound has been reported. With this compound, however, it is difficult to attain high efficiency.

Korean Patent Publication No. 10-2006-0109524 discloses an arylphosphine oxide-based compound, an arylphosphine sulfide-based compound or an arylphosphine selenide-based compound and an organic electroluminescence device using the same, but is problematic because high efficiency cannot be obtained in a pure-blue phosphorescent device.

Applied Physics Letter (Appl. Phys. Lett. 92, 083308, 2008) discloses a blue phosphorescent device using a phosphine oxide compound having a fluorene structure, but the quantum efficiency of the device is only about 9%, undesirably resulting in low device efficiency.

As conventional compounds having high triplet energy, a variety of carbazole-based compounds have been developed. The carbazole-based compounds have been applied to various phosphorescent devices because of high triplet energy thereof, but are problematic because electron injection characteristics may deteriorate, undesirably limiting diverse applications thereof. In the case where an aromatic structure is introduced to improve thermal stability, triplet energy may decrease, undesirably resulting in limited applications.

Accordingly, with the goal of overcoming the problems of the conventional organic material having high triplet energy, the present invention is intended to develop a novel host material, namely, a phosphine-based compound having a carbazole structure, and to apply it as the host material of a light-emitting layer of an organic electroluminescence device.

DISCLOSURE

Technical Problem

In order to solve problems of low efficiency of conventional organic electroluminescence devices, the present invention adopts a highly efficient carbazole-based compound, which is configured such that an aromatic structure is provided at the center thereof and includes at least two carbazole units and at least one phosphine unit, and thus which may exhibit high thermal stability and high triplet energy and may adjust balance between electrons and holes and thereby may be applied as a host material for any light-emitting layer from red to blue phosphorescence, and furthermore may achieve high efficiency characteristics in a pure-blue phosphorescent device, and thus an object of the present invention is to provide a highly efficient carbazole-based compound and an organic electroluminescence device including the same.

Technical Solution

The present invention provides a compound for an organic electroluminescence device, represented by Chemical Formula 1 below.

[Chemical Formula 1]

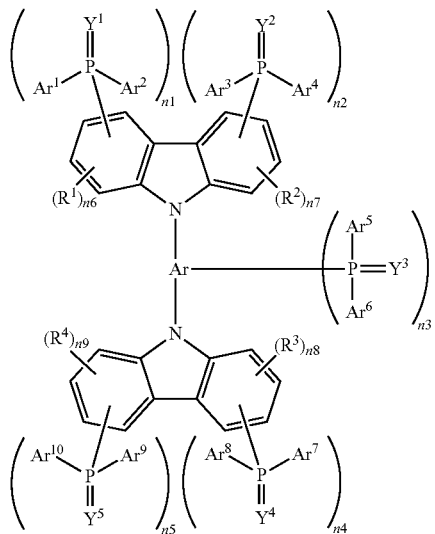

[Chemical Formula 2]

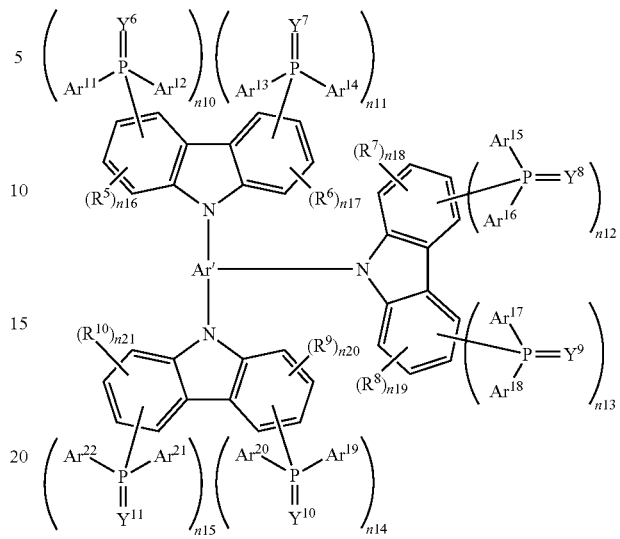

In Chemical Formula 1, Ar represents a substituted or unsubstituted aryl group having 6 to 50 ring carbons, or a substituted or unsubstituted heteroaryl group having 5 to 50 ring atoms, $Y^1$ to $Y^5$ are independently an oxygen atom, a sulfur atom or a selenium atom, $Ar^1$ to $Ar^{10}$ are identical or different substituents and each represent a substituted or unsubstituted aryl group having 6 to 50 ring carbons, or a substituted or unsubstituted heteroaryl group having 5 to 50 ring atoms, $R^1$ to $R^4$ each represent a unit which does not expand a conjugated structure of a carbazole unit, and part or all of $R^1$ to $R^4$ are independently a hydrogen atom, or $R^1$ to $R^4$ are identical or different substituents and each represent a halogen atom, a cyano group, a nitro group, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the group suitable for substitution on the Ar, $Ar^1$ to $Ar^{10}$, and $R^1$ to $R^4$ is identical or different and represents a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons, n1 to n5 are independently 0 or 1, n1+n2+n3+n4+n5≠0, and n6 to n9 are independently 0 or 1.

In addition, the present invention provides a compound for an organic electroluminescence device, represented by Chemical Formula 2 below.

In Chemical Formula 2, Ar' represents a substituted or unsubstituted aryl group having 6 to 50 ring carbons, or a substituted or unsubstituted heteroaryl group having 5 to 50 ring atoms, $Y^6$ to $Y^{11}$ are independently an oxygen atom, a sulfur atom or a selenium atom, $Ar^{11}$ to $Ar^{22}$ are identical or different substituents and each represent a substituted or unsubstituted aryl group having 6 to 50 ring carbons, or a substituted or unsubstituted heteroaryl group having 5 to 50 ring atoms, $R^5$ to $R^{10}$ each represent a unit which does not expand a conjugated structure of a carbazole unit, and part or all of $R^5$ to $R^{10}$ are independently a hydrogen atom, or $R^5$ to $R^{10}$ are identical or different substituents and each represent a halogen atom, a cyano group, a nitro group, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the group suitable for substitution on the Ar', $Ar^{11}$ to $Ar^{22}$, and $R^5$ to $R^{10}$ is identical or different and represents a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons, n10 to n15 are independently 0 or 1, n10+n11+n12+n13+n14+n15≠0, and n16 to n21 are independently 0 or 1.

In addition, the present invention provides an organic electroluminescence device, comprising a first electrode; a second electrode; and a light-emitting layer including a host and a dopant, wherein the host includes the compound for an organic electroluminescence device of claim 1 or 4.

In addition, the present invention provides an organic electroluminescence device, comprising a first electrode; a second electrode; a light-emitting layer; an electron transport layer; and a hole transport layer, wherein the hole transport layer includes the compound for an organic electroluminescence device of claim 1 or 4.

Advantageous Effects

According to the present invention, a highly efficient carbazole-based compound is configured such that an aromatic structure is provided at the center thereof and at least two carbazole units and at least one phosphine unit are included in the aromatic structure, so that this compound can exhibit high thermal stability and high triplet energy and can adjust balance between electrons and holes and thereby can be applied as a host material having high efficiency characteristics for a light-emitting layer for red to blue phosphorescence, in particular, pure-blue phosphorescence.

According to the present invention, an organic electroluminescence device includes the highly efficient carbazole-based compound of the invention, thus exhibiting superior efficiency characteristics in a red to blue phosphorescent device, in particular, a pure-blue phosphorescent device.

BEST MODE

Figure 1:
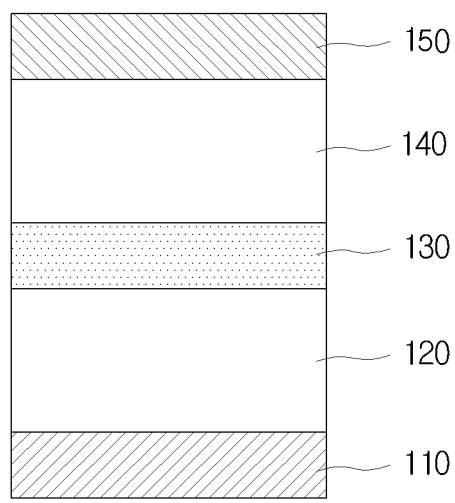
FIG. 1 is a schematic view showing the structure of an organic electroluminescence device according to the present invention.
Figure 2:
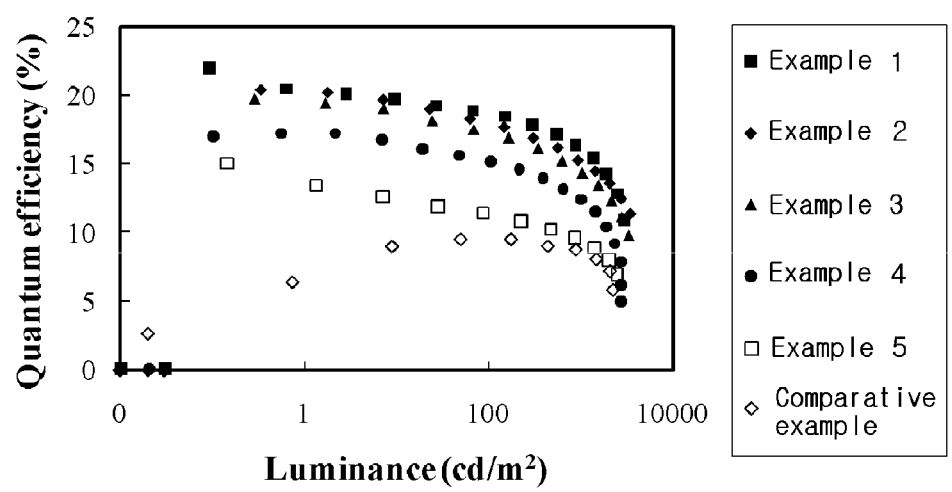
FIG. 2 is a schematic view showing the efficiency and the luminance of the example according to the present invention and a comparative example.

Hereinafter, a detailed description will be given of a highly efficient carbazole-based compound and an organic electroluminescence (EL) device including the same according to preferred embodiments of the present invention with reference to the following chemical formulas or the appended drawings.

Below is a description of a highly efficient carbazole-based compound according to the present invention and an organic EL device including the same.

The present invention provides a compound for an organic EL device, as represented by Chemical Formula 1 below.

[Chemical Formula 1]

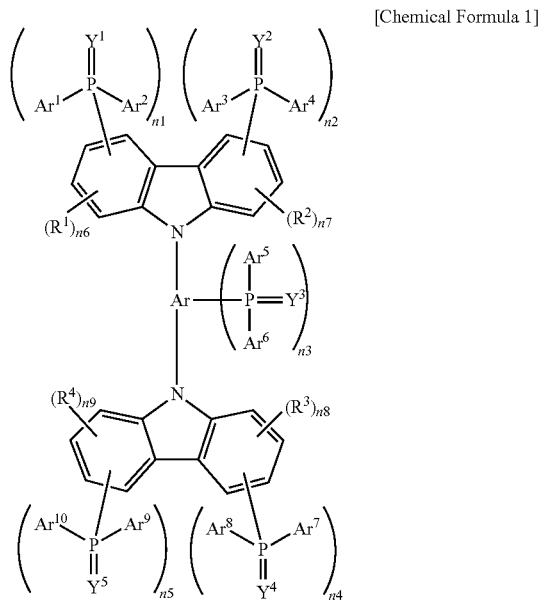

In Chemical Formula 1, Ar represents a substituted or unsubstituted aryl group having 6 to 50 ring carbons, or a substituted or unsubstituted heteroaryl group having 5 to 50 ring atoms, $Y^1$ to $Y^5$ are independently an oxygen atom, a sulfur atom or a selenium atom, $Ar^1$ to $Ar^{10}$ are identical or different substituents and each represent a substituted or unsubstituted aryl group having 6 to 50 ring carbons, or a substituted or unsubstituted heteroaryl group having 5 to 50 ring atoms, $R^1$ to $R^4$ each represent a unit which does not expand a conjugated structure of a carbazole unit, and part or all of $R^1$ to $R^4$ are independently a hydrogen atom, or $R^1$ to $R^4$ are identical or different substituents and each represent a halogen atom, a cyano group, a nitro group, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the group suitable for substitution on the Ar, $Ar^1$ to $Ar^{10}$, and $R^1$ to $R^4$ is identical or different and represents a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons, n1 to n5 are independently 0 or 1, n1+n2+n3+n4+n5≠0, and n6 to n9 are independently 0 or 1.

According to the present invention, there may be provided the compound for an organic EL device, as represented by Chemical Formula 1 in which Ar represents a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, a substituted or unsubstituted pyrenyl group, substituted or unsubstituted dibenzofuran, substituted or unsubstituted dibenzothiophene, substituted or unsubstituted dibenzophosphole, substituted or unsubstituted dibenzophosphole oxide, substituted or unsubstituted benzofuran, substituted or unsubstituted benzothiophene, substituted or unsubstituted carbazole, substituted or unsubstituted phenylcarbazole, substituted or unsubstituted indole, substituted or unsubstituted phenylindole, substituted or unsubstituted pyridine, substituted or unsubstituted pyridazine, or substituted or unsubstituted pyrimidine, $Y^1$ to $Y^5$ are an oxygen atom, $Ar^1$ to $Ar^{10}$ are identical or different substituents and each represent a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, $R^1$ to $R^4$ each represent a unit which does not expand a conjugated structure of a carbazole unit, and part or all of $R^1$ to $R^4$ are independently a hydrogen atom, or $R^1$ to $R^4$ are identical or different substituents and each represent a halogen atom, a cyano group, a nitro group, tert-butyl, substituted or unsubstituted triphenylmethyl, substituted or unsubstituted diphenylmethyl, substituted or unsubstituted phenylmethyl, methylsilyl, substituted or unsubstituted triphenylsilyl, methyl, ethyl, or propyl, wherein the group suitable for substitution on the Ar, $Ar^1$ to $Ar^{10}$, and $R^1$ to $R^4$ is identical or different and represents a halogen atom, a cyano group, a nitro group, an aryl group having 6 to 34 ring carbons, a heteroaryl group having 5 to 34 ring atoms, an alkyl group having 1 to 34 carbons, a cycloalkyl group having 3 to 34 carbons, a thio group having 1 to 34 carbons, or a silyl group having 1 to 34 carbons, n1 to n5 are independently 0 or 1, n1+n2+n3+n4+n5≠0, and n6 to n9 are independently 0 or 1.

According to the present invention, there may be provided the compound for an organic EL device, as represented by Chemical Formula 1 in which Ar is a phenyl group, $Y^1$ to $Y^5$ are an oxygen atom, $Ar^1$ to $Ar^{10}$ each represent a phenyl group, $R^1$ to $R^4$ each represent a hydrogen atom, n1 to n5 are independently 0 or 1, n1+n2+n3+n4+n5≠0, and n6 to n9 are independently 0 or 1.

The present invention provides a compound for an organic EL device, as represented by Chemical Formula 2 below.

[Chemical Formula 2]

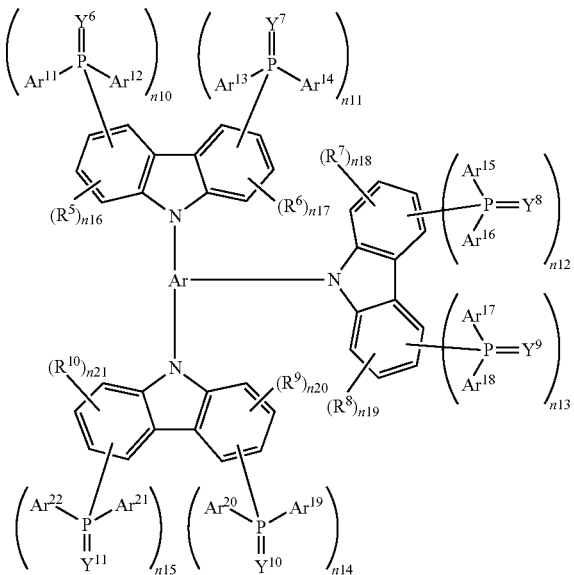

In Chemical Formula 2, Ar' represents a substituted or unsubstituted aryl group having 6 to 50 ring carbons, or a substituted or unsubstituted heteroaryl group having 5 to 50 ring atoms, $Y^6$ to $Y^{11}$ are independently an oxygen atom, a sulfur atom or a selenium atom, $Ar^{11}$ to $Ar^{22}$ are identical or different substituents and each represent a substituted or unsubstituted aryl group having 6 to 50 ring carbons, or a substituted or unsubstituted heteroaryl group having 5 to 50 ring atoms, $R^5$ to $R^{10}$ each represent a unit which does not expand a conjugated structure of a carbazole unit, and part or all of $R^5$ to $R^{10}$ are independently a hydrogen atom, or $R^5$ to $R^{10}$ are identical or different substituents and each represent a halogen atom, a cyano group, a nitro group, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein the group suitable for substitution on the Ar', $Ar^{11}$ to $Ar^{22}$, and $R^5$ to $R^{10}$ is identical or different and represents a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons, n10 to n15 are independently 0 or 1, n10+n11+n12+n13+n14+n15≠0, and n16 to n21 are independently 0 or 1.

According to the present invention, there may be provided the compound for an organic EL device, as represented by Chemical Formula 2 in which Ar' represents a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, substituted or unsubstituted phenylcarbazole, substituted or unsubstituted phenylindole, substituted or unsubstituted pyrenyl, substituted or unsubstituted pyridine, substituted or unsubstituted pyridazine, or substituted or unsubstituted pyrimidine, $Y^6$ to $Y^{11}$ are an oxygen atom, $Ar^{11}$ to $Ar^{22}$ are identical or different substituents and each represent a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, $R^5$ to $R^{10}$ each represent a unit which does not expand a conjugated structure of a carbazole unit, and part or all of $R^5$ to $R^{10}$ are independently a hydrogen atom, or $R^5$ to $R^{10}$ are identical or different substituents and each represent a halogen atom, a cyano group, a nitro group, tert-butyl, substituted or unsubstituted triphenylmethyl, substituted or unsubstituted diphenylmethyl, substituted or unsubstituted phenylmethyl, methylsilyl, substituted or unsubstituted triphenylsilyl, methyl, ethyl, or propyl, wherein the group suitable for substitution on the Ar', $Ar^{11}$ to $Ar^{22}$, and $R^5$ to $R^{10}$ is identical or different and represents a halogen atom, a cyano group, a nitro group, an aryl group having 6 to 34 ring carbons, a heteroaryl group having 5 to 34 ring atoms, an alkyl group having 1 to 34 carbons, a cycloalkyl group having 3 to 34 carbons, a thio group having 1 to 34 carbons, or a silyl group having 1 to 34 carbons, n10 to n15 are independently 0 or 1, n10+n11+n12+n13+n14+n15≠0, and n16 to n21 are independently 0 or 1.

According to the present invention, there may be provided the compound for an organic EL device, as represented by Chemical Formula 2 in which Ar' represents a phenyl group, $Y^6$ to $Y^{11}$ are an oxygen atom, $Ar^{11}$ to $Ar^{22}$ each represent a phenyl group, $R^5$ to $R^{10}$ each represent a hydrogen atom, n10 to n15 are independently 0 or 1, n10+n11+n12+n13+n14+n15≠0, and n16 to n21 are independently 0 or 1.

Specific examples of the substituted or unsubstituted aryl group having 6 to 50 ring carbons on the Ar, Ar', and $Ar^1$ to $Ar^{22}$ include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-tert-butylphenyl, p-(2-phenylpropyl)phenyl, 3-methyl-2-naphthyl, 4-methyl-1-naphthyl, 4-methyl-1-anthryl, 4-methylbiphenylyl or 4-tert-butyl-p-terphenyl-4-yl.

Specific examples of the aromatic heterocyclic group having 5 to 50 ring atoms on the Ar, Ar', and $Ar^1$ to $Ar^{22}$ include 1-pyrolyl, 2-pyrolyl, 3-pyrolyl, pyrazinyl, pyrimidyl, pyridazyl, 2-pyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 1-dibenzofuranyl, 2-dibenzofuranyl, 3-dibenzofuranyl, 6-dibenzofuranyl, 7-dibenzofuranyl, 8-dibenzofuranyl, 9-dibenzofuranyl, 2-benzothiophene, 3-benzothiophene, 4-benzothiophene, 5-benzothiophene, 6-benzothiophene, 7-benzothiophene, 1-dibenzothiophene, 2-dibenzothiophene, 3-dibenzothiophene, 4-dibenzothiophene, 6-dibenzothiophene, 7-dibenzothiophene, 8-dibenzothiophene, 9-dibenzothiophene, 2-benzophosphole, 3-benzophosphole, 4-benzophosphole, 5-benzophosphole, 6-benzophosphole, 7-benzophosphole, 1-dibenzophosphole, 2-dibenzophosphole, 3-dibenzophosphole, 4-dibenzophosphole, 6-dibenzophosphole, 7-dibenzophosphole, 8-dibenzophosphole, 9-dibenzophosphole, 2-benzophosphole oxide, 3-benzophosphole oxide, 4-benzophosphole oxide, 5-benzophosphole oxide, 6-benzophosphole oxide, 7-benzophosphole oxide, 1-dibenzophosphole oxide, 2-dibenzophosphole oxide, 3-dibenzophosphole oxide, 4-dibenzophosphole oxide, 6-dibenzophosphole oxide, 7-dibenzophosphole oxide, 8-dibenzophosphole oxide, 9-dibenzophosphole oxide, qunolyl, 3-qunolyl, 4-qunolyl, 5-qunolyl, 6-qunolyl, 7-qunolyl, 8-qunolyl, 1-isoqunolyl, 3-isoqunolyl, 4-isoqunolyl, 5-isoqunolyl, 6-isoqunolyl, 7-isoqunolyl, 8-isoqunolyl, 2-quinoxalinyl, 5-quinoxalinyl, 6-quinoxalinyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 1,7-phenanthrolin-2-yl, 1,7-phenanthrolin-3-yl, 1,7-phenanthrolin-4-yl, 1,7-phenanthrolin-5-yl, 1,7-phenanthrolin-6-yl, 1,7-phenanthrolin-8-yl, 1,7-phenanthrolin-9-yl, 1,7-phenanthrolin-10-yl, 1,8-phenanthrolin-2-yl, 1,8-phenanthrolin-3-yl, 1,8-phenanthrolin-4-yl, 1,8-phenanthrolin-5-yl, 1,8-phenanthrolin-6-yl, 1,8-phenanthrolin-7-yl, 1,8-phenanthrolin-9-yl, 1,8-phenanthrolin-10-yl, 1,9-phenanthrolin-2-yl, 1,9-phenanthrolin-3-yl, 1,9-phenanthrolin-4-yl, 1,9-phenanthrolin-5-yl, 1,9-phenanthrolin-6-yl, 1,9-phenanthrolin-7-yl, 1,9-phenanthrolin-8-yl, 1,9-phenanthrolin-10-yl, 1,10-phenanthrolin-2-yl, 1,10-phenanthrolin-3-yl, 1,10-phenanthrolin-4-yl, 1,10-phenanthrolin-5-yl, 2,9-phenanthrolin-1-yl, 2,9-phenanthrolin-3-yl, 2,9-phenanthrolin-4-yl, 2,9-phenanthrolin-5-yl, 2,9-phenanthrolin-6-yl, 2,9-phenanthrolin-7-yl, 2,9-phenanthrolin-8-yl, 2,9-phenanthrolin-10-yl, 2,8-phenanthrolin-1-yl, 2,8-phenanthrolin-3-yl, 2,8-phenanthrolin-4-yl, 2,8-phenanthrolin-5-yl, 2,8-phenanthrolin-6-yl, 2,8-phenanthrolin-7-yl, 2,8-phenanthrolin-9-yl, 2,8-phenanthrolin-10-yl, 2,7-phenanthrolin-1-yl, 2,7-phenanthrolin-3-yl, 2,7-phenanthrolin-4-yl, 2,7-phenanthrolin-5-yl, 2,7-phenanthrolin-6-yl, 2,7-phenanthrolin-8-yl, 2,7-phenanthrolin-9-yl, 2,7-phenanthrolin-10-yl, 1-phenazinyl, 2-phenazinyl, 1-phenothiazinyl, 2-phenothiazinyl, 3-phenothiazinyl, 4-phenothiazinyl, 10-phenothiazinyl, 1-phenoxazinyl, 2-phenoxazinyl, 3-phenoxazinyl, 4-phenoxazinyl, 10-phenoxazinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrol-1-yl, 2-methylpyrol-3-yl, 2-methylpyrol-4-yl, 2-methylpyrol-5-yl, 3-methylpyrol-1-yl, 3-methylpyrol-2-yl, 3-methylpyrol-4-yl, 3-methylpyrol-5-yl, 2-tert-butylpyrol-4-yl, 3-(2-phenylpropyl)pyrol-1-yl, 2-methyl-1-indolyl, 4-methyl-1-indolyl, 2-methyl-3-indolyl, 4-methyl-3-indolyl, 2-tert-butyl-1-indolyl, 4-tert-butyl-1-indolyl, 2-tert-butyl-3-indolyl or 4-tert-butyl-3-indolyl.

On the $R^1$ to $R^{10}$, specific examples of the substituted or unsubstituted alkyl group having 1 to 50 carbons and the substituted or unsubstituted cycloalkyl group having 3 to 50 carbons include methyl, ethyl, n-propyl, n-pentyl, n-butyl, n-hexyl, n-heptyl, n-octyl, n-decanyl, n-eicosanyl isopropyl, sec-butyl, isobutyl, tert-butyl, hydroxymethyl, 1-hydroxyethyl, 2-hydroxyethyl, 2-hydroxyisobutyl, 1,2-dihydroxyethyl, 1,3-dihydroxyisopropyl, 2,3-dihydroxy-tert-butyl, 1,2,3-trihydroxypropyl, chloromethyl, 1-chloroethyl, 2-chloroethyl, 2-chloroisobutyl, 1,2-dichloroethyl, 1,3-dichloroisopropyl, 2,3-dichloro-tert-butyl, 1,2,3-trichloropropyl, bromomethyl, 1-bromoethyl, 2-bromoethyl, 2-bromoisobutyl, 1,2-dibromoethyl, 1,3-dibromoisopropyl, 2,3-dibromo-tert-butyl, 1,2,3-tribromopropyl, iodomethyl, 1-iodoethyl, 2-iodoethyl, 2-iodoisobutyl, 1,2-diiodoethyl, 1,3-diiodoisopropyl, 2,3-diiodo-tert-butyl, 1,2,3-triiodopropyl, aminomethyl, 1-aminoethyl, 2-aminoethyl, 2-aminoisobutyl, 1,2-diaminoethyl, 1,3-diaminoisopropyl, 2,3-diamino-tert-butyl, 1,2,3-triaminopropyl, cyanomethyl, 1-cyanoethyl, 2-cyanoethyl, 2-cyanoisobutyl, 1,2-dicyanoethyl, 1,3-dicyanoisopropyl, 2,3-dicyano-tert-butyl, 1,2,3-tricyanopropyl, nitromethyl, 1-nitroethyl, 2-nitroethyl, 2-nitroisobutyl, 1,2-dinitroethyl, 1,3-dinitroisopropyl, 2,3-dinitro-tert-butyl, 1,2,3-trinitropropyl, phenylmethyl, diphenylmethyl, triphenylmethyl, 1-phenylethyl, 2-phenylethyl, 1,1-diphenylethyl, 1,2-diphenylethyl, 2,2-diphenylethyl, 2,2,2-triphenylethyl, 1,2,2,-triphenylethyl, 1,1,2-triphenylethyl, 1-phenyl-n-propyl, 2-phenyl-n-propyl, 3-phenyl-n-propyl, 1,1-diphenyl-n-propyl, 2,2-diphenyl-n-propyl, 3,3-diphenyl-n-propyl, 1,2-diphenyl-n-propyl, 1,3-diphenyl-n-propyl, 2,3-diphenyl-n-propyl, 3,3,3-triphenyl-n-propyl, 1,1,2-triphenyl-n-propyl, 1,2,2-triphenyl-n-propyl, 1,3,3-triphenyl-n-propyl, 1,1,3-triphenyl-n-propyl, 1-phenyl-isopropyl, 2-phenyl-isopropyl, 1,1-diphenyl-isopropyl, 2,2-diphenyl-isopropyl, 1,2-diphenyl-isopropyl, 1,3-diphenyl-isopropyl, 2,3-diphenyl-isopropyl, 1,1,1-triphenyl-isopropyl, 1,1,2-triphenyl-isopropyl, 1,1,3-triphenyl-isopropyl, 1-phenyl-n-butyl, 2-phenyl-n-butyl, 3-phenyl-n-butyl, 4-phenyl-n-butyl, 1,1-diphenyl-n-butyl, 2,2-diphenyl-n-butyl, 3,3-diphenyl-n-butyl, 4,4-diphenyl-n-butyl, 1,2-diphenyl-n-butyl, 1,3-diphenyl-n-butyl, 2,3-diphenyl-n-butyl, 4,4,4-triphenyl-n-butyl, 1,1,2-triphenyl-n-butyl, 1,2,2-triphenyl-n-butyl, 1,3,3-triphenyl-n-butyl, 1,1,3-triphenyl-n-butyl, 1-phenyl-tert-butyl, 1,1-diphenyl-tert-propyl, 1,1,1-triphenyl-tert-butyl, cyclopropyl, cyclobutyl, cyclopentyl, cyclohexyl, 4-methylcyclohexyl, 1-adamantyl, 2-adamantyl, 1-norbornyl, 2-norbornyl, etc.

On the $R^1$ to $R^{10}$, specific examples of the substituted or unsubstituted thio group having 1 to 50 carbons include methylthio, ethylthio, propylthio, butylthio, pentylthio, hexylthio, tri(isopropyl)thio, tri(isobutyl)thio, tri(tert-butyl)thio, tri(2-butyl)thio, phenylthio, naphthylthio, biphenylthio, (3-methylphenyl)thio, (4-methylnaphthyl)thio, (2-methylbiphenyl) thio, etc.

On the $R^1$ to $R^{10}$, specific examples of the substituted or unsubstituted silyl group having 1 to 50 carbons include trimethylsilyl, triethylsilyl, tributylsilyl, tri(isopropyl)silyl, tri(isobutyl)silyl, tri(tert-butyl)silyl, tri(2-butyl)silyl, triphenylsilyl, trinaphthylsilyl, tribiphenylsilyl, tri(3-methylphenyl)silyl, tri(4-methylnaphthyl)silyl, tri(2-methylbiphenyl) silyl, phenylmethylsilyl, phenylethylsilyl, naphthylmethylsilyl, naphthylethylsilyl, biphenylmethylsilyl, 3-methyl-phenylmethylsilyl, phenyl(isopropyl)silyl, naphthyl(isopropyl)silyl or biphenyl(isopropyl)silyl.

In order to solve the problems of a conventional organic material having high triplet energy, a compound was developed in the present invention, which is configured such that an aromatic structure is provided at the center thereof and at least two carbazole units and at least one phosphine oxide are included in the aromatic structure. The compound according to the present invention is featured in that an aromatic compound which may expand the conjugated structure of the carbazole unit is not introduced, thus ensuring high triplet energy, and also that electron transfer characteristics may be improved via the phosphine oxide unit, thereby maintaining balance between holes and electrons in the organic compound. Furthermore, the compound according to the present invention includes a phosphine oxide unit and a hydrogen, saturated hydrocarbon structure, etc., which do not influence on triplet energy, ultimately ensuring high triplet energy and superior thermal stability.

Below the structural formulas of Compounds 1 to 20 which are examples of the compound for an organic EL device according to the present invention are shown in Tables 1 to 3, but the present invention is not limited to such compounds.

TABLE 1

| Compound | Structural Formula |
|---|---|
| 1 | |
| 2 | |
| 3 | |
| 4 | |

TABLE 1-continued
| Compound | Structural Formula |
|---|---|
| 5 | 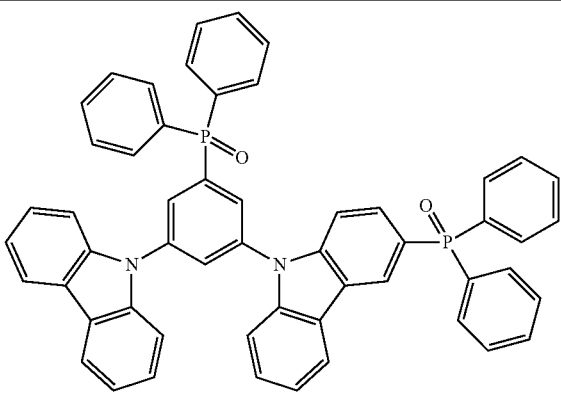 |
| 6 | 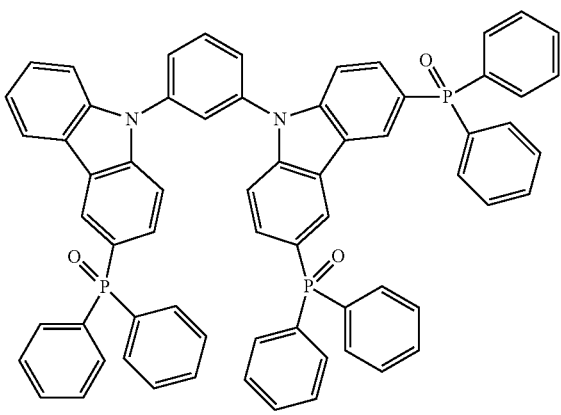 [SMILES: O=P(c1ccccc1)(c1ccccc1)c1ccc2c(c1)c1ccccc1n2-c1cccc(-n2c3ccc(P(=O)(c4ccccc4)c4ccccc4)cc3c3cc(P(=O)(c4ccccc4)c4ccccc4)ccc32)c1] |
| 7 | 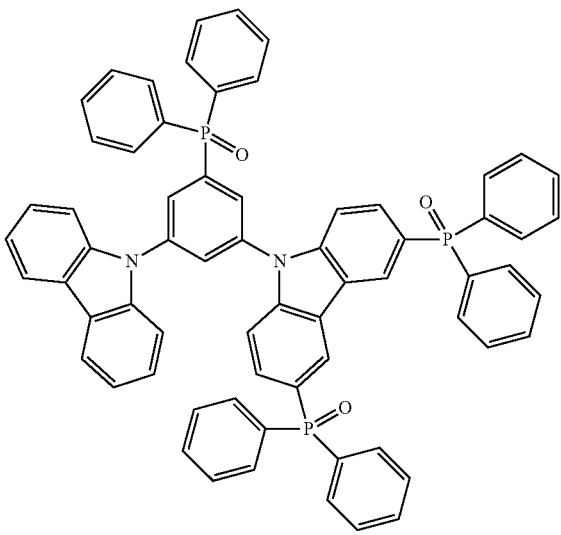 [SMILES: O=P(c1ccccc1)(c1ccccc1)c1cc(-n2c3ccccc3c3ccccc32)cc(-n2c3ccc(P(=O)(c4ccccc4)c4ccccc4)cc3c3cc(P(=O)(c4ccccc4)c4ccccc4)ccc32)c1] |

TABLE 1-continued

| Compound | Structural Formula |
|---|---|
| 8 | |

TABLE 2

| Compound | Structural Formula |
|---|---|
| 9 | |
| 10 | |

US 9,142,784 B2
17                                                                                                    18
TABLE 2-continued
| Compound | Structural Formula |
|---|---|
| 11 | 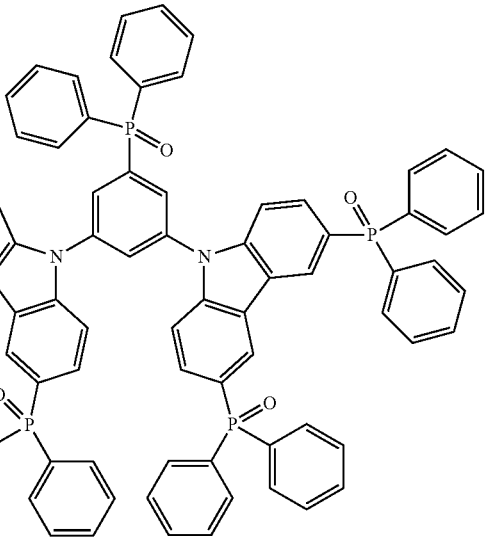 |
| 12 | 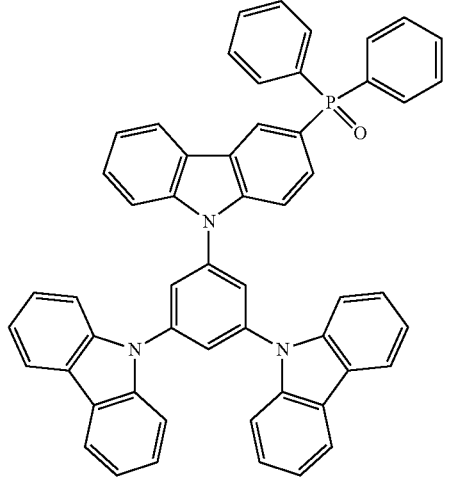 [SMILES: O=P(c1ccccc1)(c1ccccc1)c1ccc2c(c1)c1ccccc1n2-c1cc(-n2c3ccccc3c3ccccc32)cc(-n2c3ccccc3c3ccccc32)c1] |
| 13 | 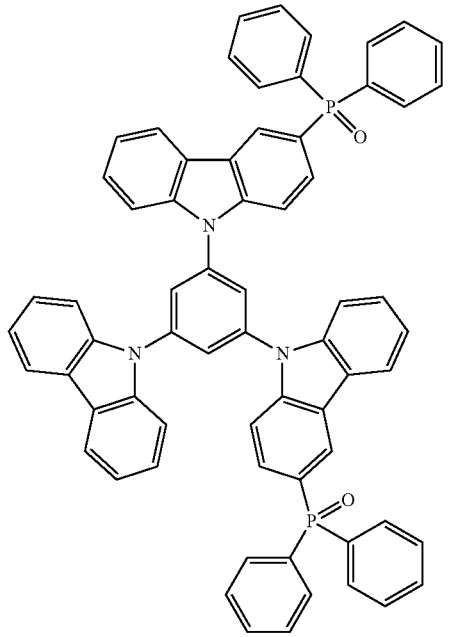 [SMILES: O=P(c1ccccc1)(c1ccccc1)c1ccc2c(c1)c1ccccc1n2-c1cc(-n2c3ccccc3c3ccccc32)cc(-n2c3ccccc3c3cc(P(=O)(c4ccccc4)c4ccccc4)ccc32)c1] |

TABLE 2-continued
| Compound | Structural Formula |
|---|---|
| 14 | 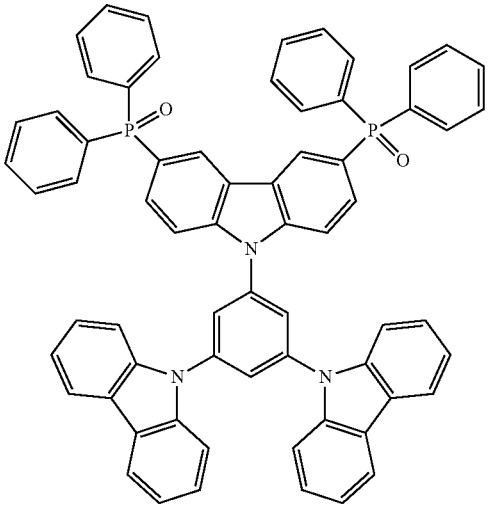 [SMILES: O=P(c1ccccc1)(c1ccccc1)c1ccc2c(c1)c1cc(P(=O)(c3ccccc3)c3ccccc3)ccc1n2-c1cc(-n2c3ccccc3c3ccccc32)cc(-n2c3ccccc3c3ccccc32)c1] |
TABLE 3
| Compound | Structural Formula |
|---|---|
| 15 | 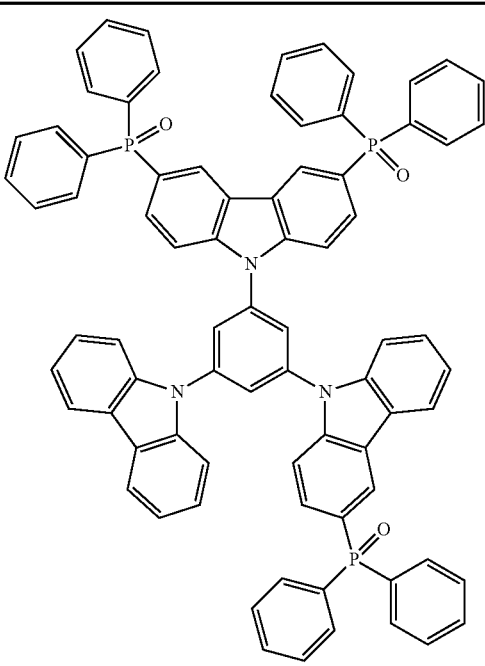 |

TABLE 3-continued
| Compound | Structural Formula |
|---|---|
| 16 | 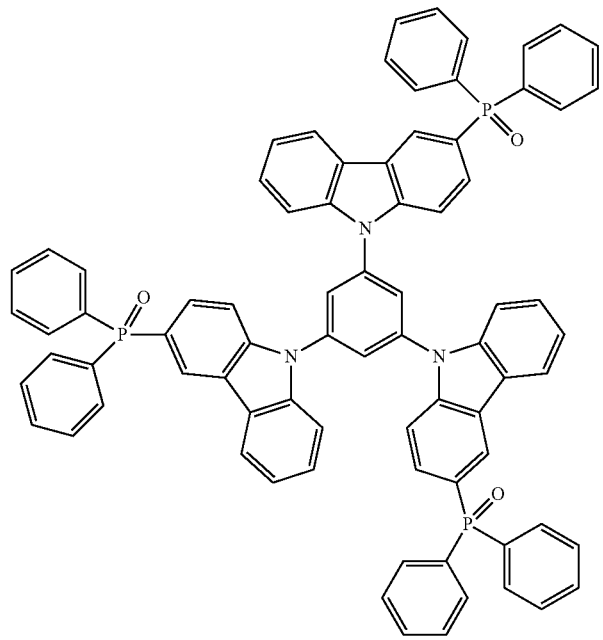 [SMILES: O=P(c1ccccc1)(c1ccccc1)c1ccc2c(c1)c1ccccc1n2-c1cc(-n2c3ccccc3c3cc(P(=O)(c4ccccc4)c4ccccc4)ccc32)cc(-n2c3ccccc3c3cc(P(=O)(c4ccccc4)c4ccccc4)ccc32)c1] |
| 17 | 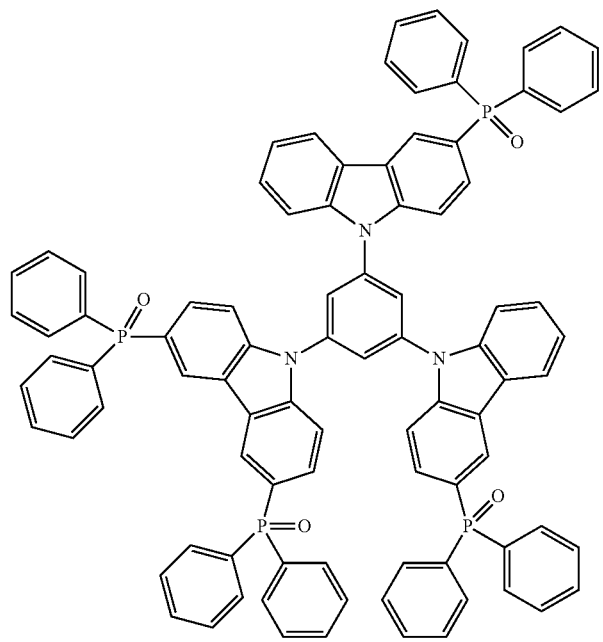 [SMILES: O=P(c1ccccc1)(c1ccccc1)c1ccc2c(c1)c1ccccc1n2-c1cc(-n2c3ccccc3c3cc(P(=O)(c4ccccc4)c4ccccc4)ccc32)cc(-n2c3ccc(P(=O)(c4ccccc4)c4ccccc4)cc3c3cc(P(=O)(c4ccccc4)c4ccccc4)ccc32)c1] |

TABLE 3-continued
| Compound | Structural Formula |
|---|---|
| 18 | 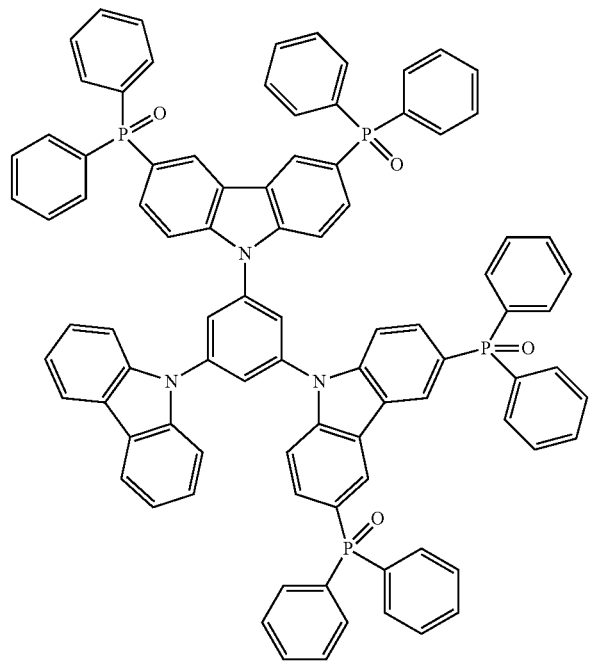 [SMILES: O=P(c1ccccc1)(c1ccccc1)c1ccc2c(c1)c1cc(P(=O)(c3ccccc3)c3ccccc3)ccc1n2-c1cc(-n2c3ccccc3c3ccccc32)cc(-n2c3ccc(P(=O)(c4ccccc4)c4ccccc4)cc3c3cc(P(=O)(c4ccccc4)c4ccccc4)ccc32)c1] |
| 19 | 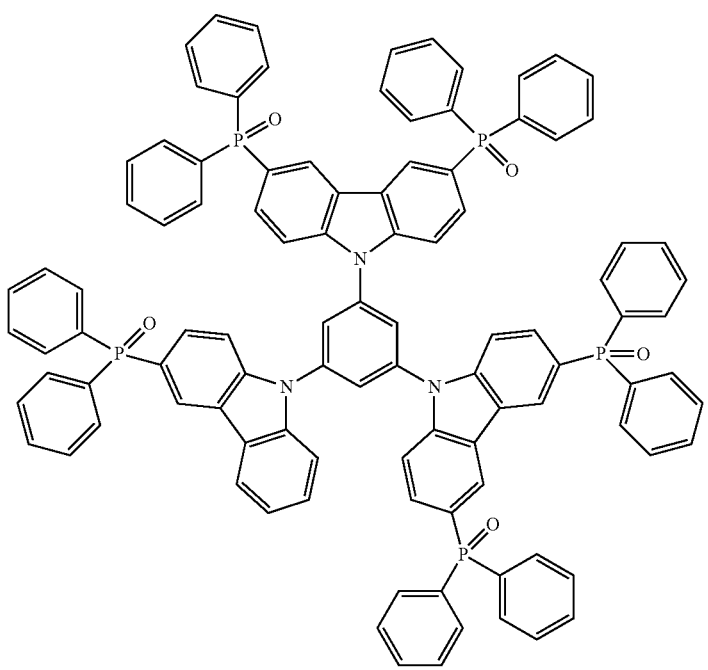 [SMILES: O=P(c1ccccc1)(c1ccccc1)c1ccc2c(c1)c1ccccc1n2-c1cc(-n2c3ccc(P(=O)(c4ccccc4)c4ccccc4)cc3c3cc(P(=O)(c4ccccc4)c4ccccc4)ccc32)cc(-n2c3ccc(P(=O)(c4ccccc4)c4ccccc4)cc3c3cc(P(=O)(c4ccccc4)c4ccccc4)ccc32)c1] |

TABLE 3-continued

| Compound | Structural Formula |
| --- | --- |
| 20 | |
| 30 | |

With reference to the appended drawings, the organic EL device according to the present invention is described below. FIG. 1 schematically shows the structure of the organic EL device according to the present invention. The organic EL device including the compound represented by Chemical Formula 1 or 2 may be embodied in a variety of structures.

According to an embodiment of the present invention, the organic EL device includes a first electrode 110; a second electrode 150; and a light-emitting layer 130 including a host and a dopant, wherein the host includes the compound for an organic EL device according to the present invention.

According to the present invention, the organic EL device may further include an electron transport layer 140 and a hole transport layer 120.

In the present invention, the hole transport layer 120 or the electron transport layer 140 may include the compound for an organic EL device according to the present invention.

In an organic EL device according to the present invention including a first electrode 110; a second electrode 150; a light-emitting layer 130; an electron transport layer 140; and a hole transport layer 120, the electron transport layer 140 or the hole transport layer 120 includes the compound for an organic EL device according to the present invention.

In the present invention, the organic EL device further includes one or more layers selected from among a hole injection layer, an electron injection layer, and an electron transport layer, thus increasing luminous efficiency.

The organic EL device is preferably supported on a transparent substrate. The material for the transparent substrate is not particularly limited so long as it has good mechanical strength, thermal stability and transparency. Specific examples thereof include glass, a transparent plastic film, etc.

The anode material of the organic EL device according to the present invention may include a metal having a work function of 4 eV or more, an alloy, an electrical conductive compound, or a mixture thereof. Specific examples thereof include Au metal or a transparent conductive material such as CuI, ITO (Indium Tin Oxide), $SnO_2$ and ZnO. The thickness of the anode film may be 10 to 200 nm.

The cathode material of the organic EL device according to the present invention may include a metal having a work function of less than 4 eV, an alloy, an electrical conductive compound, or a mixture thereof. Specific examples thereof include Na, Na—K alloy, Ca, Mg, Li, Li alloy, In, Al, Mg alloy, Al alloy, etc. In addition, Al/$AlO_2$, Al/Li, Mg/Ag or Mg/In may be used. The thickness of the cathode film may be 10 to 200 nm. In order to increase the luminous efficiency of the organic EL device, one or more electrodes should have a light transmittance of 10% or more. The sheet resistance of the electrodes is preferably hundreds of Ω/mm or less. The thickness of the electrodes may range from 10 nm to 1 μm, and preferably from 10 to 400 nm. Such electrodes may be obtained by forming the above electrode material into a thin film using vapor deposition such as chemical vapor deposition (CVD) or physical vapor deposition (PVD) or sputtering.

Also, the hole transport material and the hole injection material may be optionally selected from materials typically used as a hole transport material among light conductive materials and materials known to be useful for forming a hole transport layer or a hole injection layer of an organic EL device, in addition to the compound of Chemical Formula 1 or 2 according to the present invention. Examples thereof include porphyrin compound derivatives such as N,N-dicarbazolyl-3,5-benzene (mCP), poly(3,4-ethylenedioxythiophene):polystyrenesulfonate (PEDOT:PSS), N,N'-di(1-naphthyl)-N,N'-diphenylbenzidine (NPD), N,N'-diphenyl-N,N'-di(3-methylphenyl)-4,4'-diaminobiphenyl (TPD), N,N'-diphenyl-N,N'-dinaphthyl-4,4'-diaminobiphenyl, N,N,N'N'-tetra-p-tolyl-4,4'-diaminobiphenyl, N,N,N',N'-tetraphenyl-4,4'-diaminobiphenyl, copper (II) 1,10,15,20-tetraphenyl-21H, 23H-porphyrin, etc., triarylamine derivatives including polymers having aromatic tertiary amines on the main chains or side chains thereof, 1,1-bis(4-di-p-tolylaminophenyl)cyclohexane, N,N,N-tri(p-tolyl)amine, 4,4',4'-tris[N-(3-methylphenyl)-N-phenylamino]triphenylamine, etc., carbazole derivatives including N-phenylcarbazole and polyvinylcarbazole, phthalocyanine derivatives including nonmetallic phthalocyanine, copper phthalocyanine, etc., starbust amine derivatives, enamine stilbene derivatives, derivatives of aromatic tertiary amines and styryl amine compounds, and polysilane.

Known electron transport materials for the electron transport layer include, for example, diphenylphosphine oxide-4-(triphenylsilyl)phenyl (TSPO1), $Alq_3$, a 2,5-diaryl silole derivative (PyPySPyPy), a perfluorinated compound (PF-6P), octasubstituted cyclooctatetraene compounds (COTS), etc., which may be used in mixtures.

In the organic EL device according to the present invention, the electron injection layer, the electron transport layer, the hole injection layer and the hole transport layer may be provided in the form of a single layer containing one or more kinds of the above compounds, or of a laminated plurality of layers containing different kinds of compounds.

Another light-emitting material employed in the organic EL device according to the present invention may include known light-emitting materials, for example, photoluminescent fluorescent materials, fluorescent brighteners, laser dyes, organic scintillators, and fluorescent analysis reagents. Specific examples thereof include carbazole-based compounds, phosphine oxide-based compounds, carbazole-based phosphine oxide compounds, polyaromatic compounds including bis((3,5-difluoro-4-cyanophenyl)pyridine)iridium picolinate (FCNIrpic), tris(8-hydroxyquinoline)aluminum ($Alq_3$), anthracene, phenanthrene, pyrene, crysene, perylene, coronene, rubrene and quinacridone, oligophenylene compounds including quaterphenyl, scintillators for liquid scintillation including 1,4-bis(2-methylstyryl)benzene, 1,4-bis(4-methylstyryl)benzene, 1,4-bis(4-methyl-5-phenyl-2-oxazolyl)benzene, 1,4-bis(5-phenyl-2-oxazolyl)benzene, 2,5-bis(5-t-butyl-2-benzoxazolyl)thiophene, 1,4-diphenyl-1,3-butadiene, 1,6-diphenyl-1,3,5-hexatriene, 1,1,4,4-tetraphenyl-1,3-butadiene, etc., metal complexes of oxine derivatives, coumarin dyes, dicyanomethylenepyrane dyes, dicyanomethylenethiopyrane dyes, polymethine dyes, oxobenzanthracene dyes, xanthene dyes, carbostyryl dyes, perylene dyes, oxazine compounds, stilbene derivatives, spiro compounds, oxadiazole compounds, etc.

Respective layers of the organic EL device according to the present invention may be provided in the form of a thin film using a known process such as vacuum deposition, spin coating or casting, or may be prepared using materials therefor. The film thickness of respective layers is not particularly limited, and may be appropriately determined depending on the characteristics of the materials, and may be typically set in the range of 2 nm to 5000 nm.

Because the compound of Chemical Formula 1 or 2 according to the present invention may be subjected to vacuum deposition, it may be simply formed into a thin film and may be easily provided in the form of a uniform thin film having almost no pin holes.

The preparation of the compounds for an organic EL device according to the present invention and the organic EL devices including the same is described in more detail via the following examples, which are merely illustrative but the scope of the present invention is not limited thereto.

EXAMPLE

According to the present invention, compounds for an organic EL device were prepared, and organic EL devices were manufactured using the same. The following preparation examples and examples are set to illustrate the present invention but are not construed to limit the present invention.

In the present invention, a blue phosphorescent device was manufactured using the above compound, and the characteristics of the organic compound were evaluated.

Preparation Example 1

Synthesis of Intermediate 4 g of carbazole, 8.08 g of 1-bromo-3-iodobenzene, 13.2 g of potassium carbonate, 3.08 g of copper powder and 0.63 g of dibenzo-18-crown-6 were dissolved in 30 mL of o-dichlorobenzene, and the resulting solution was refluxed at a steady 100° C. After completion of the reaction, the reaction mixture was extracted with dichloromethane and distilled water, and the solvent was dried. The resulting solid was filtered and purified, yielding 9-(3-bromophenyl)-9H-carbazole as an intermediate.

Preparation Example 2

Synthesis of Intermediate 0.31 g of 9-(3-bromophenyl)-9H-carbazole, 0.2 g of 3-bromo-9-carbazole, 0.44 g of potassium carbonate, 0.1 g of copper powder and 0.02 g of dibenzo-18-crown-6 were dissolved in 10 mL of o-dichlorobenzene, and the resulting solution was refluxed at a steady 100° C. After completion of the reaction, the reaction mixture was extracted with dichloromethane and distilled water, and the solvent was dried. The resulting solid was filtered and purified, yielding 9-(3-(9H-carbazol-9-yl)phenyl)-3-bromo-9H-carbazole as an intermediate.

Preparation Example 3

Synthesis of Intermediate 6.56 g of 3-bromo-9H-carbazole, 4 g of 1,3-diiodobenzene, 13.4 g of potassium carbonate, 3.08 g of copper powder and 0.64 g of dibenzo-18-crown-6 were dissolved in 45 mL of o-dichlorobenzene, and the resulting solution was refluxed at a steady 100° C. After completion of the reaction, the reaction mixture was extracted with dichloromethane and distilled water, and the solvent was dried. The resulting solid was filtered and purified, yielding 1,3-bis(3-bromo-9H-carbazol-9-yl)benzene as an intermediate.

Preparation Example 4

Synthesis of Intermediate 4.75 g of 9-(3-bromophenyl)-9H-carbazole, 4 g of 3,6-dibromo-9-carbazole, 6.8 g of potassium carbonate, 1.56 g of copper powder and 0.97 g of dibenzo-18-crown-6 were dissolved in 40 mL of o-dichlorobenzene, and the resulting solution was refluxed at a steady 100° C. After completion of the reaction, the reaction mixture was extracted with dichloromethane and distilled water, and the solvent was dried. The resulting solid was filtered and purified, yielding 9-(3-(9H-carbazol-9-yl)phenyl)-3,6-dibromo-9H-carbazole as an intermediate.

Preparation Example 5

Synthesis of Intermediate 1 g of 1,3,5-tribromobenzene was added to 20 mL of tetrahydrofuran and the temperature was adjusted to −78° C. Subsequently, 1.65 mL of butyllithium was slowly added dropwise. The mixture was stirred for 2 hr while maintaining its temperature, and 0.45 g of chlorotrimethylsilane was slowly added dropwise, after which the temperature of the mixture was raised to room temperature. After completion of the reaction, triethylamine and methanol were added, and the reaction mixture was stirred and extracted, followed by drying the solvent. The resulting solid was filtered and purified, yielding (3,5-dibromophenyl)trimethylsilane as an intermediate.

Preparation Example 6

Synthesis of Intermediate 1.19 g of 9H-carbazole, 1 g of (3,5-dibromophenyl)trimethylsilane, 3.57 g of potassium carbonate, 0.82 g of copper powder and 0.17 g of dibenzo-18-crown-6 were dissolved in 20 mL of o-dichlorobenzene, and the resulting solution was refluxed at a steady 100° C. After completion of the reaction, the reaction mixture was extracted with dichloromethane and distilled water, and the solvent was dried. The resulting solid was filtered and purified, yielding 9,9'-(5-(trimethylsilyl)-1,3-phenylene)bis(9H-carbazole) as an intermediate.

Preparation Example 7

Synthesis of Intermediate 1 g of 9,9'-(5-(trimethylsilyl)-1,3-phenylene)bis(9H-carbazole) and 0.40 g of N-bromosuccinimide were dissolved in 20 mL of dimethylformamide, and then the reaction was carried out at room temperature. After completion of the reaction, the reaction mixture was extracted with dichloromethane and distilled water, and the solvent was dried. The resulting solid was filtered and purified, yielding 9,9'-(5-bromo-1,3-phenylene)bis(9H-carbazole) as an intermediate.

Preparation Example 8

Synthesis of Intermediate 1.00 g of 9,9'-(5-bromo-1,3-phenylene)bis(9H-carbazole), 0.65 g of 3-bromo-9H-carbazole, 1.13 g of potassium carbonate, 0.26 g of copper powder and 0.05 g of dibenzo-18-crown-6 were dissolved in 20 mL of o-dichlorobenzene, and the resulting solution was refluxed at a steady 100° C. After completion of the reaction, the reaction mixture was extracted with dichloromethane and distilled water, and the solvent was dried. The resulting solid was filtered and purified, yielding 9,9'-(5-(3-bromo-9H-carbazol-9-yl)-1,3-phenylene)bis(9H-carbazole) as an intermediate.

Preparation Example 9

Synthesis of Compound 1

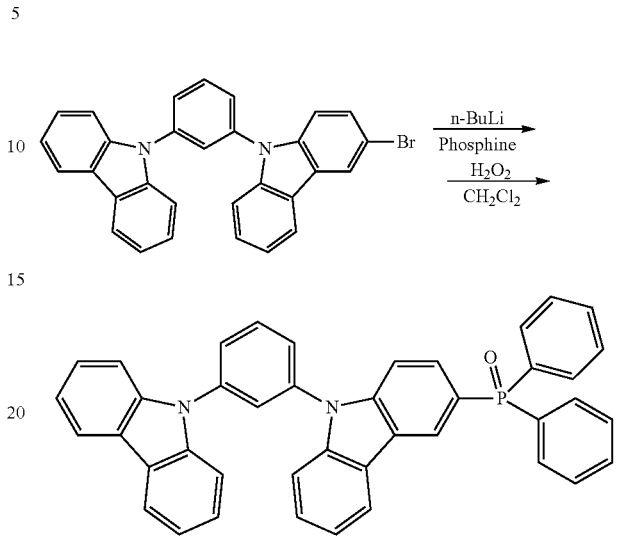

30 mL of tetrahydrofuran was added to 2 g of 9-(3-(9H-carbazol-9-yl)phenyl)-3-bromo-9H-carbazole and the temperature was adjusted to −78° C. Subsequently, 2.13 mL of butyllithium was slowly added dropwise. While maintaining the temperature, the mixture was stirred for 2 hr, and 1.17 g of chlorodiphenylphosphine was slowly added dropwise, after which the temperature of the mixture was raised to room temperature. After completion of the reaction, methanol was added, and the reaction mixture was stirred and extracted, followed by drying the solvent. To the resulting solid was added dichloromethane, and while the mixture was being stirred, a small amount of hydrogen peroxide was added, yielding 9-(3-(9H-carbazol-9-yl)phenyl)-3-(diphenylphosphonyl)-9H-carbazole (mCPPO1) as white phosphine oxide.

Nuclear magnetic resonance analysis and mass spectrometry were performed, and the results were as follows.

NMR-1H (200 MHz, CDCl3): δ8.61-8.55 (d, 2H), 8.17-8.09 (dd, 3H), 7.91-7.64 (m, 10H), 7.58-7.39 (m, 9H), 7.36-7.31 (m, 3H), 7.27-7.25 (d, 2H).

MS (FAB) m/z 608 [(M+1)$^+$].

Preparation Example 10

Synthesis of Compound 2

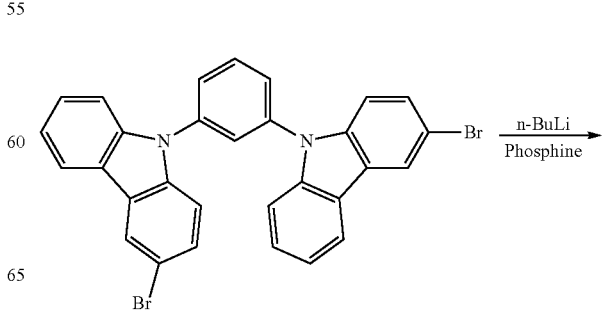

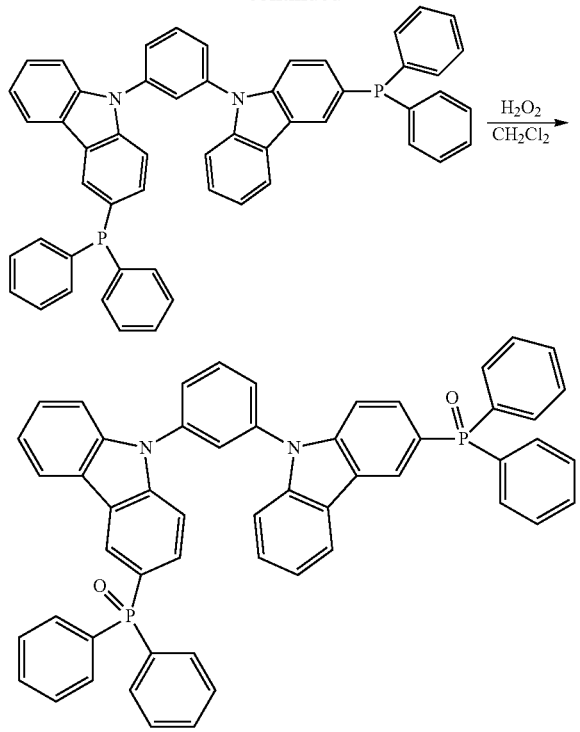

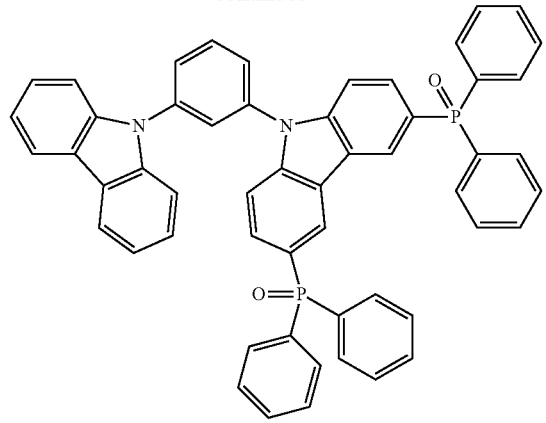

30 mL of tetrahydrofuran was added to 2 g of 1,3-bis(3-bromo-9H-carbazol-9-yl)benzene and the temperature was adjusted to −78° C. Subsequently, 3.53 mL of butyllithium was slowly added dropwise. While maintaining the temperature, the mixture was stirred for 2 hr, and 1.94 g of chlorodiphenylphosphine was slowly added dropwise, after which the temperature of the mixture was raised to room temperature. After completion of the reaction, methanol was added, and the reaction mixture was stirred and extracted, followed by drying the solvent. To the resulting solid was added dichloromethane, and while the mixture was being stirred, a small amount of hydrogen peroxide was added, yielding 1,3-bis(3-(diphenylphosphonyl)-9H-carbazol-9-yl)benzene (mCPPO2) as white phosphine oxide.

Nuclear magnetic resonance analysis and mass spectrometry were performed, and the results were as follows.

NMR-1H (200 MHz, CDCl3): δ8.60-8.54 (d, 2H), 8.13-8.09 (d, 2H), 7.92-7.63 (m, 14H), 7.58-7.47 (m, 18H), 7.37-7.30 (m, 2H)

MS (FAB) m/z 808 [(M+1)$^+$].

Preparation Example 11

Synthesis of Compound 3

30 mL of tetrahydrofuran was added to 2.06 g of 9-(3-(9H-carbazol-9-yl)phenyl)-3,6-dibromo-9H-carbazole and the temperature was adjusted to −78° C. Subsequently, 3.63 mL of butyllithium was slowly added dropwise. While maintaining the temperature, the mixture was stirred for 2 hr, and 2.00 g of chlorodiphenylphosphine was slowly added dropwise, after which the temperature of the mixture was raised to room temperature. After completion of the reaction, methanol was added, and the reaction mixture was stirred and extracted, followed by drying the solvent. To the resulting solid was added dichloromethane, and while the mixture was being stirred, a small amount of hydrogen peroxide was added, yielding 9-(3-(9H-carbazol-9-yl)phenyl)-3,6-bis(diphenylphosphonyl)-9H-carbazole (mCPPO3) having the structure of the represented chemical formula as white phosphine oxide.

NMR-1H (200 MHz, CDCl3): δ8.50-8.44 (d, 2H), 8.16-8.12 (d, 2H), 7.92-7.64 (m, 14H), 7.60-7.38 (m, 18H), 7.34-7.30 (dd, 2H).

MS (FAB) m/z 808 [(M+1)$^+$].

Preparation Example 12

Synthesis of Compound 4

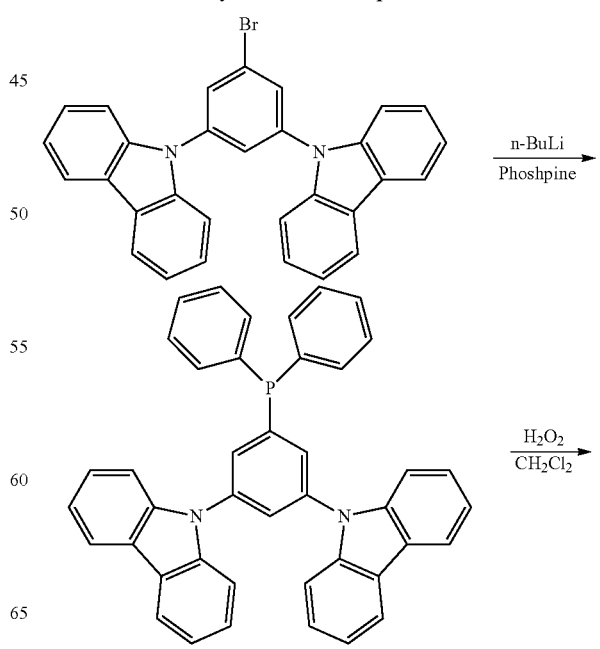

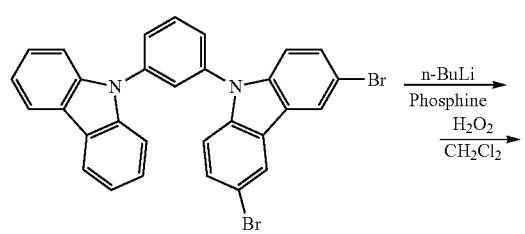

-continued

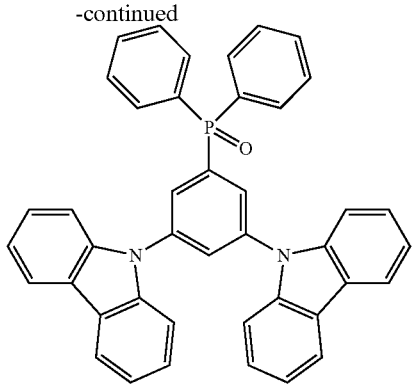

20 mL of tetrahydrofuran was added to 1.00 g of 9,9'-(5-bromo-1,3-phenylene)bis(9H-carbazole) and the temperature was adjusted to −78° C. Subsequently, 1.06 mL of butyllithium was slowly added dropwise. While maintaining the temperature, the mixture was stirred for 2 hr, and 0.58 g of chlorodiphenylphosphine was slowly added dropwise, after which the temperature of the mixture was raised to room temperature. After completion of the reaction, methanol was added, and the reaction mixture was stirred and extracted, followed by drying the solvent. To the resulting solid was added dichloromethane, and while the mixture was being stirred, a small amount of hydrogen peroxide was added, yielding 9,9'-(5-(diphenylphosphonyl)-1,3-phenylene)bis(9H-carbazole) (mCPPO4) as white phosphine oxide.

Nuclear magnetic resonance analysis and mass spectrometry were performed, and the results were as follows.

NMR-1H (200 MHz, CDCl3): δ8.55-8.50 (d, 2H), 8.12-8.04 (dd, 3H), 7.98-7.54 (m, 10H), 7.45-7.39 (m, 9H), 7.36-7.30 (m, 3H), 7.25-7.21 (d, 2H).

MS (FAB) m/z 608 [(M+1)+]

Preparation Example 13

Synthesis of Compound 12

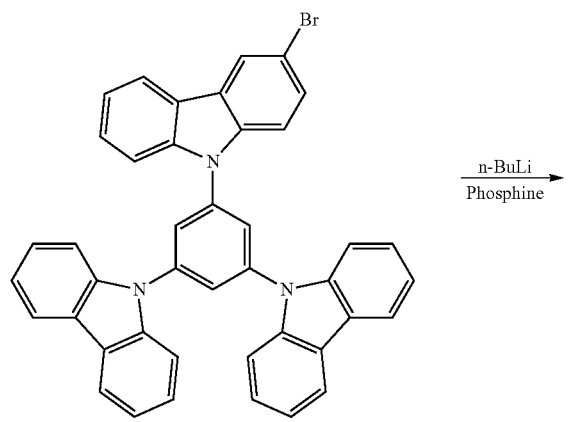

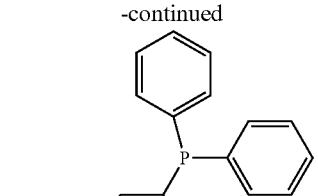

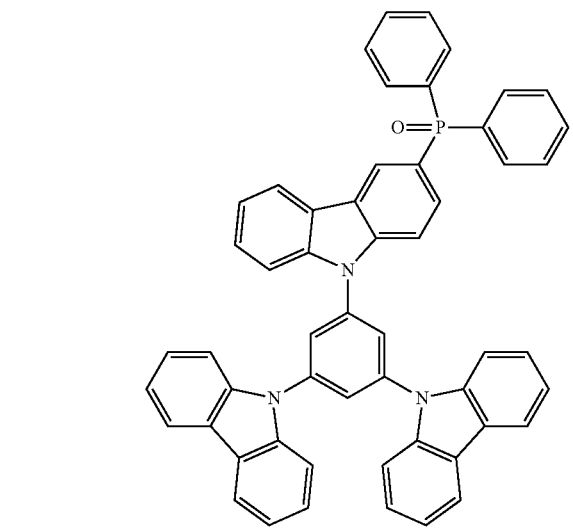

20 mL of tetrahydrofuran was added to 1.00 g of 9,9'-(5-(3-bromo-9H-carbazol-9-yl)-1,3-phenylene)bis(9H-carbazole) and the temperature was adjusted to −78° C. Subsequently, 0.74 mL of butyllithium was slowly added dropwise. While maintaining the temperature, the mixture was stirred for 2 hr, and 0.43 g of chlorodiphenylphosphine was slowly added dropwise, after which the temperature of the mixture was raised to room temperature. After completion of the reaction, methanol was added, and the reaction mixture was stirred and extracted, followed by drying the solvent. To the resulting solid was added dichloromethane, and while the mixture was being stirred, a small amount of hydrogen peroxide was added, yielding 9,9'-(5-(3-(diphenylphosphonyl)-9H-carbazol-9-yl)-1,3-phenylene)bis(9H-carbazole) as white phosphine oxide corresponding to Compound 12.

Nuclear magnetic resonance analysis and mass spectrometry were performed, and the results were as follows.

NMR-1H (200 MHz, CDCl3): δ8.55-8.49 (d, 2H), 8.12-8.07 (d, 2H), 7.94-7.64 (m, 14H), 7.60-7.38 (m, 16H), 7.33-7.29 (dd, 2H).

MS (FAB) m/z 773 [(M+1)+].

Example 1

A blue phosphorescent device including Compound 1, that is, mCPPO1, synthesized in the present invention was formed using FCNIrpic which is a known blue dopant.

In order to apply the present compound as a host, a blue phosphorescent device was manufactured using FCNIrpic which is a blue dopant.

The structure of the device was ITO/N,N'-diphenyl-N,N'-bis-[4-(phenyl-m-tolyl-amino)-phenyl]-biphenyl-4,4'-diamine (DNTPD, 60 nm)/NPD (20 nm)/mCP (10 nm)/mCPPO1:FCNIrpic (30 nm, 3%)/TSPO1 (20 nm)/LiF/Al.

The device was manufactured in the following manner. Specifically, an ITO substrate was washed using ultrasound for 30 min in pure water and isopropyl alcohol, and the surface of the ITO substrate was treated using short-wavelength UV light, after which an organic material was vacuum-deposited thereon at a pressure of $1 \times 10^{-6}$ torr. DNTPD, NPD, mCP, and TSPO1 were deposited at a rate of 0.1 nm/s, thus forming respective films having the corresponding thicknesses, and Compound 1 was vacuum-deposited together with a FCNIr dopant. As such, Compound 1 was deposited at a rate of 0.1 nm/s, and FCNIr was deposited at a rate of 0.03 nm/s. LiF was formed to a thickness of 1 nm at a rate of 0.01 nm/s, and Al was formed to a thickness of 100 nm at a deposition rate of 0.5 nm/s. The device thus obtained was sealed using a CaO desiccant and a cover glass.

The quantum efficiency of Examples 1, 2, 3, 4, 5 and Comparative Example 1 was measured in accordance with the description of literature by Forrest (G. Gu and S. R. Forrest, IEEE Journal of Selected Topics in Quantum Electronics, Vol. 4, No. 1, January/February 1998, p. 83-99).

The blue organic EL device manufactured in the present invention manifested a maximum quantum efficiency of 21.9%. The color coordinates were (0.14, 0.17). The maximum quantum efficiency and the color coordinates of Examples 1 to 5 according to the present invention and Comparative Example 1 are shown in Table 4 below.

Example 2

A blue phosphorescent device including Compound 2, that is, mCPPO2, synthesized in the present invention was formed using FCNIrpic which is a known blue dopant.

The structure of the device was ITO/DNTPD (60 nm)/NPD (20 nm)/mCP (10 nm)/mCPPO2:FCNIrpic (30 nm, 3%)/TSPO1 (20 nm)/LiF/Al. The device was manufactured in the same manner as in Example 1, with the exception that Compound 2 was used in lieu of Compound 1.

The blue organic EL device manufactured in the present invention manifested a maximum quantum efficiency of 20.3%. The color coordinates were (0.14, 0.17).

Example 3

A blue phosphorescent device including Compound 3, that is, mCPPO3, synthesized in the present invention was formed using FCNIrpic which is a known blue dopant.

The structure of the device was ITO/DNTPD (60 nm)/NPD (20 nm)/mCP (10 nm)/mCPPO3:FCNIrpic (30 nm, 3%)/TSPO1 (20 nm)/LiF/Al. The device was manufactured in the same manner as in Example 1, with the exception that Compound 3 was used in lieu of Compound 1.

The blue organic EL device manufactured in the present invention manifested a maximum quantum efficiency of 19.7%. The color coordinates were (0.14, 0.17).

Example 4

A blue phosphorescent device including Compound 4, that is, mCPPO4, synthesized in the present invention was formed using FCNIrpic which is a known blue dopant.

The structure of the device was ITO/DNTPD (60 nm)/NPD (20 nm)/mCP (10 nm)/mCPPO4:FCNIrpic (30 nm, 3%)/TSPO1 (20 nm)/LiF/Al. The device was manufactured in the same manner as in Example 1, with the exception that Compound 4 was used in lieu of Compound 1.

The blue organic EL device manufactured in the present invention manifested a maximum quantum efficiency of 17.0%. The color coordinates were (0.14, 0.17).

Example 5

A blue phosphorescent device including Compound 12, that is, mCPPO12, synthesized in the present invention was formed using FCNIrpic which is a known blue dopant.

The structure of the device was ITO/DNTPD (60 nm)/NPD (20 nm)/mCP (10 nm)/mCPPO12:FCNIrpic (30 nm, 3%)/TSPO1 (20 nm)/LiF/Al. The device was manufactured in the same manner as in Example 1, with the exception that Compound 12 was used in lieu of Compound 1.

The blue organic EL device manufactured in the present invention manifested a maximum quantum efficiency of 15.0%. The color coordinates were (0.14, 0.17).

Comparative Example 1

A typically known device having the structure of ITO/DNTPD (60 nm)/NPD (20 nm)/mCP (10 nm)/mCP:FCNIrpic (30 nm, 15%)/TSPO1 (20 nm)/LiF/Al was manufactured.

The device was manufactured in the same manner as in Example 1, with the exception that a blue phosphorescent material mCP was used instead of Compound 1 as the host material for a light-emitting layer.

This blue phosphorescent device manifested a low quantum efficiency of 9.5%. The color coordinates were (0.15, 0.19).

TABLE 4

|  | Quantum Efficiency (%) | Color Coordinates |
| --- | --- | --- |
| Ex. 1 | 21.9 | (0.14, 0.17) |
| Ex. 2 | 20.3 | (0.14, 0.17) |
| Ex. 3 | 19.7 | (0.14, 0.17) |
| Ex. 4 | 17.0 | (0.14, 0.17) |
| Ex. 5 | 15.0 | (0.14, 0.17) |
| Comp. Ex. 1 | 9.5 | (0.15, 0.19) |

INDUSTRIAL APPLICABILITY

According to the present invention, a highly efficient carbazole-based compound is configured such that an aromatic structure is provided at the center thereof and at least two carbazole units and at least one phosphine unit are included in the aromatic structure, and thereby this compound can exhibit high thermal stability and high triplet energy and can adjust balance between electrons and holes and thereby can be applied as a host material having high efficiency characteristics for a light-emitting layer for red to blue phosphorescence, in particular, pure-blue phosphorescence.

According to the present invention, an organic EL device includes the highly efficient carbazole-based compound of the invention, thus exhibiting superior efficiency characteristics in a red to blue phosphorescent device, in particular, a pure-blue phosphorescent device.

The invention claimed is:

1. A compound for an organic electroluminescence device, represented by Chemical Formula 1 below:

[Chemical Formula 1]

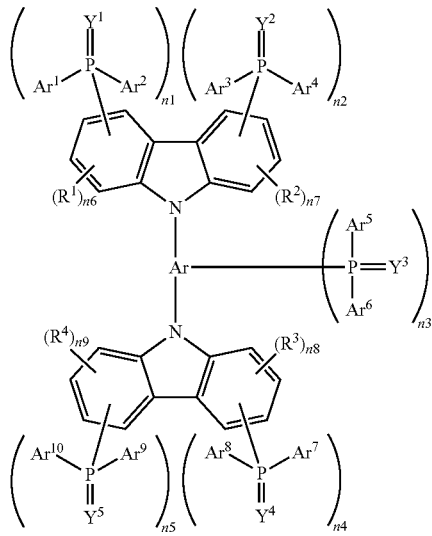

wherein Ar represents a substituted or unsubstituted aryl group having 6 to 50 ring carbons, or a substituted or unsubstituted heteroaryl group having 5 to 50 ring atoms, $Y^1$ to $Y^5$ are independently an oxygen atom, a sulfur atom or a selenium atom, $Ar^1$ to $Ar^{10}$ are identical or different substituents and each represent a substituted or unsubstituted aryl group having 6 to 50 ring carbons, or a substituted or unsubstituted heteroaryl group having 5 to 50 ring atoms, $R^1$ to $R^4$ each represent a unit which does not expand a conjugated structure of a carbazole unit, and part or all of $R^1$ to $R^4$ are independently a hydrogen atom, or $R^1$ to $R^4$ are identical or different substituents and each represent a halogen atom, a cyano group, a nitro group, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein a group suitable for substitution on the Ar, $Ar^1$ to $Ar^{10}$, and $R^1$ to $R^4$ is identical or different and represents a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons, n1 to n5 are independently 0 or 1, n1+n2+n3+n4+n5≠0, and n6 to n9 are independently 0 or 1.

2. The compound of claim 1, wherein in Chemical Formula 1, Ar represents a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, a substituted or unsubstituted pyrenyl group, substituted or unsubstituted dibenzofuran, substituted or unsubstituted dibenzothiophene, substituted or unsubstituted dibenzophosphole, substituted or unsubstituted dibenzophosphole oxide, substituted or unsubstituted benzofuran, substituted or unsubstituted benzothiophene, substituted or unsubstituted carbazole, substituted or unsubstituted phenylcarbazole, substituted or unsubstituted indole, substituted or unsubstituted phenylindole, substituted or unsubstituted pyridine, substituted or unsubstituted pyridazine, or substituted or unsubstituted pyrimidine, $Y^1$ to $Y^5$ are an oxygen atom, $Ar^1$ to $Ar^{10}$ are identical or different substituents and each represent a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, $R^1$ to $R^4$ each represent a unit which does not expand a conjugated structure of a carbazole unit, and part or all of $R^1$ to $R^4$ are independently a hydrogen atom, or $R^1$ to $R^4$ are identical or different substituents and each represent a halogen atom, a cyano group, a nitro group, tert-butyl, substituted or unsubstituted triphenylmethyl, substituted or unsubstituted diphenylmethyl, substituted or unsubstituted phenylmethyl, methylsilyl, substituted or unsubstituted triphenylsilyl, methyl, ethyl, or propyl, wherein the group suitable for substitution on the Ar, $Ar^1$ to $Ar^{10}$, and $R^1$ to $R^4$ is identical or different and represents a halogen atom, a cyano group, a nitro group, an aryl group having 6 to 34 ring carbons, a heteroaryl group having 5 to 34 ring atoms, an alkyl group having 1 to 34 carbons, a cycloalkyl group having 3 to 34 carbons, a thio group having 1 to 34 carbons, or a silyl group having 1 to 34 carbons, n1 to n5 are independently 0 or 1, n1+n2+n3+n4+n5≠0, and n6 to n9 are independently 0 or 1.

3. The compound of claim 1, wherein in Chemical Formula 1, Ar is a phenyl group, $Y^1$ to $Y^5$ are an oxygen atom, $Ar^1$ to $Ar^{10}$ each represent a phenyl group, $R^1$ to $R^4$ each represent a hydrogen atom, n1 to n5 are independently 0 or 1, n1+n2+n3+n4+n5≠0, and n6 to n9 are independently 0 or 1.

4. A compound for an organic electroluminescence device, represented by Chemical Formula 2 below:

[Chemical Formula 2]

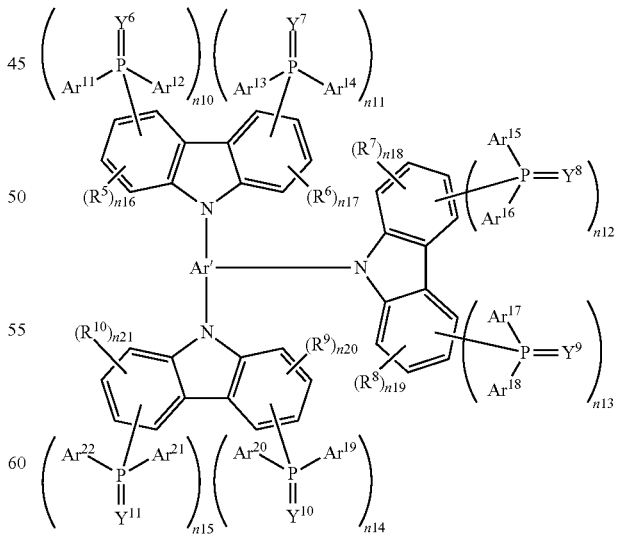

wherein Ar' represents a substituted or unsubstituted aryl group having 6 to 50 ring carbons, or a substituted or unsubstituted heteroaryl group having 5 to 50 ring atoms, $Y^6$ to $Y^{11}$ are independently an oxygen atom, a sulfur atom or a selenium atom, $Ar^{11}$ to $Ar^{22}$ are identical or different substituents and each represent a substituted or unsubstituted aryl group having 6 to 50 ring carbons, or a substituted or unsubstituted heteroaryl group having 5 to 50 ring atoms, $R^5$ to $R^{10}$ each represent a unit which does not expand a conjugated structure of a carbazole unit, and part or all of $R^5$ to $R^{10}$ are independently a hydrogen atom, or $R^5$ to $R^{10}$ are identical or different substituents and each represent a halogen atom, a cyano group, a nitro group, a substituted or unsubstituted alkyl group having 1 to 50 carbons, a substituted or unsubstituted cycloalkyl group having 3 to 50 carbons, a substituted or unsubstituted thio group having 1 to 50 carbons, or a substituted or unsubstituted silyl group having 1 to 50 carbons, wherein a group suitable for substitution on the Ar', $Ar^{11}$ to $Ar^{22}$, and $R^5$ to $R^{10}$ is identical or different and represents a halogen atom, a cyano group, a nitro group, an aryl group having 6 to 50 ring carbons, a heteroaryl group having 5 to 50 ring atoms, an alkyl group having 1 to 50 carbons, a cycloalkyl group having 3 to 50 carbons, a thio group having 1 to 50 carbons, or a silyl group having 1 to 50 carbons, n10 to n15 are independently 0 or 1, n10+n11+n12+n13+n14+n15≠0, and n16 to n21 are independently 0 or 1.

5. The compound of claim 4, wherein in Chemical Formula 2, Ar' represents a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, substituted or unsubstituted phenylcarbazole, substituted or unsubstituted phenylindole, substituted or unsubstituted pyrenyl, substituted or unsubstituted pyridine, substituted or unsubstituted pyridazine, or substituted or unsubstituted pyrimidine, $Y^6$ to $Y^{11}$ are an oxygen atom, $Ar^{11}$ to $Ar^{22}$ are identical or different substituents and each represent a substituted or unsubstituted phenyl group having 6 to 34 carbons, a substituted or unsubstituted biphenyl group, a substituted or unsubstituted terphenyl group, a substituted or unsubstituted naphthyl group, a substituted or unsubstituted anthryl group, or a substituted or unsubstituted pyrenyl group, $R^5$ to $R^{10}$ each represent a unit which does not expand a conjugated structure of a carbazole unit, and part or all of $R^5$ to $R^{10}$ are independently a hydrogen atom, or $R^5$ to $R^{10}$ are identical or different substituents and each represent a halogen atom, a cyano group, a nitro group, tert-butyl, substituted or unsubstituted triphenylmethyl, substituted or unsubstituted diphenylmethyl, substituted or unsubstituted phenylmethyl, methylsilyl, substituted or unsubstituted triphenylsilyl, methyl, ethyl, or propyl, wherein the group suitable for substitution on the Ar', $Ar^{11}$ to $A^{22}$, and $R^5$ to $R^{10}$ is identical or different and represents a halogen atom, a cyano group, a nitro group, an aryl group having 6 to 34 ring carbons, a heteroaryl group having 5 to 34 ring atoms, an alkyl group having 1 to 34 carbons, a cycloalkyl group having 3 to 34 carbons, a thio group having 1 to 34 carbons, or a silyl group having 1 to 34 carbons, n10 to n15 are independently 0 or 1, n10+n11+n12+n13+n14+n15≠0, and n16 to n21 are independently 0 or 1.

6. The compound of claim 4, wherein in Chemical Formula 2, Ar' represents a phenyl group, $Y^6$ to $Y^{11}$ are an oxygen atom, $Ar^{11}$ to $Ar^{22}$ each represent a phenyl group, $R^5$ to $R^{10}$ each represent a hydrogen atom, n10 to n15 are independently 0 or 1, n10+n11+n12+n13+n14+n15≠0, and n16 to n21 are independently 0 or 1.

7. An organic electroluminescence device, comprising:

a first electrode; a second electrode; and a light-emitting layer including a host and a dopant, wherein the host includes the compound for an organic electroluminescence device of claim 1.

8. The organic electroluminescence device of claim 7, further comprising an electron transport layer; and a hole transport layer.

9. The organic electroluminescence device of claim 8, wherein the hole transport layer or the electron transport layer includes the compound for an organic electroluminescence device of claim 1.

10. An organic electroluminescence device, comprising:

a first electrode; a second electrode; a light-emitting layer; an electron transport layer; and a hole transport layer, wherein the hole transport layer or the electron transport layer includes the compound for an organic electroluminescence device of claim 1.

11. The organic electroluminescence device of claim 10, further comprising one or more layers selected from among a hole injection layer and an electron injection layer.

* * * * *